United States Patent
Copes

(10) Patent No.: US 7,335,818 B2
(45) Date of Patent: Feb. 26, 2008

(54) INBRED CANTALOUPE LINE I446

(75) Inventor: Bill Copes, Sacramento, CA (US)

(73) Assignee: Harris Moran Seed Company, Modesto, CA (US)

( * ) Notice: Subject to any disclaimer, the term of this patent is extended or adjusted under 35 U.S.C. 154(b) by 147 days.

(21) Appl. No.: 11/055,456

(22) Filed: Feb. 10, 2005

(65) Prior Publication Data

US 2006/0179510 A1    Aug. 10, 2006

(51) Int. Cl.
*A01H 5/00*    (2006.01)
*A01H 5/10*    (2006.01)
*A01H 4/00*    (2006.01)
*A01H 1/00*    (2006.01)
*C12N 15/82*   (2006.01)

(52) U.S. Cl. ............. 800/309; 800/260; 800/278; 800/279; 800/300; 800/301; 800/302; 800/303; 435/410

(58) Field of Classification Search ........ 800/260, 800/265, 266, 267, 274, 278, 300, 301, 302, 800/309; 435/410, 421, 430, 430.1
See application file for complete search history.

(56) References Cited

U.S. PATENT DOCUMENTS

| | | | | |
|---|---|---|---|---|
| 5,304,719 | A * | 4/1994 | Segebart | 800/303 |
| 5,367,109 | A * | 11/1994 | Segebart | 800/320.1 |
| 5,763,755 | A * | 6/1998 | Carlone | 800/320.1 |
| 5,777,196 | A | 7/1998 | Hall | |
| 5,850,009 | A * | 12/1998 | Kevern | 800/271 |
| 5,948,957 | A | 9/1999 | Chapko et al. | |
| 5,969,212 | A | 10/1999 | Getschman | |
| 2003/0177539 | A1* | 9/2003 | Copes | 800/309 |

OTHER PUBLICATIONS

Poehlman, J.M. and Sleper, D.A. Breeding Field Crops, 4th Ed. (1995), Iowa State University Press, Ames, Iowa, p. 473.

Adelberg, J.W., et al., 1994. Explant origin affects the frequency of tetraploid plants from tissue culture of melon. HortScience 29(6):689-692.

Bennetzen, et al., 1992. Approaches and progress in the molecular cloning of plant disease resistance genes, In Genetic Engeneering. 14:99-124, Ed. J.K. Setlow, Plenum Press, NY.

DeBolle, et al., 1996. Antimicrobial peptides from *Mirabilis jalapa and Amaranthus candatus*: expression, processing, localization and biological activity in transgenic tobacco. Plant Molec. Biol. 31:993-1008.

Ezura, et al., 1994. Ploidy of somatic embryos and the ability to regenerate plantlets in melons (*Cucumis melo* L.). Plant Cell Reports 14:107-111.

Kraft, et al., 2000. Linkage disequilibrium and fingerprinting in sugar beet. Theor. Appl. Genet. 101:323-326.

Pang, et al., 1992. Expression of a gene encoding a scorpion insectotoxin peptide in yeast, bacteria and plants. Gene 116:165-172.

Zhang, et al., 1996. Development of geneic male-sterile watermelon lines with delayed-green seedling marker. HortScience 31(1):123-126.

\* cited by examiner

*Primary Examiner*—David H. Kruse
*Assistant Examiner*—Keith O. Robinson
(74) *Attorney, Agent, or Firm*—Jondle & Associates, P.C.

(57) ABSTRACT

An inbred cantaloupe line, designated I446, a hybrid cantaloupe designated I446*I444, and a hybrid cantaloupe designated I446*I407 are disclosed. The invention relates to the seeds of inbred cantaloupe line I446, of hybrid cantaloupe I446*I444, and of hybrid cantaloupe I446*I407, to the plants and plant parts of inbred cantaloupe line I446, of hybrid cantaloupe I446*I444, and of hybrid cantaloupe I446*I407 and to methods for producing a cantaloupe plant, either inbred or hybrid, by crossing the inbred line I446 with itself or another cantaloupe line. The invention further relates to methods for producing a cantaloupe plant containing in its genetic material one or more transgenes and to the transgenic plants produced by that method and to methods for producing other inbred cantaloupe lines derived from the inbred I446.

19 Claims, No Drawings

INBRED CANTALOUPE LINE I446

BACKGROUND OF THE INVENTION

The present invention relates to a new and distinctive cantaloupe inbred line, designated I446, a hybrid cantaloupe designated I446*I444, and a hybrid cantaloupe designated I446*I407. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as sugar levels, small cavity size, flesh color or texture, rind firmness or strong net, resistance to diseases and insects, and tolerance to drought and heat.

Practically speaking, all cultivated forms of cantaloupe belong to the highly polymorphic species *Cucumis melo* L. that is grown for its sweet edible fruit. The term cantaloupe, as used herein, refers to the American usage of the term which is used to describe the netted melons commonly referred to as cantaloupe or muskmelon in U.S. commerce. As a crop, cantaloupes are grown commercially wherever environmental conditions permit the production of an economically viable yield. They are produced on non-climbing vines that are cultivated prostrate on the soil. On healthy plants there is a canopy of large, soft, hairy leaves, generally heart shaped and somewhat lobed. Fruits may be orange fleshed or green fleshed. The fruit surface is generally netted and roughened and in some varieties sutured. Fruit shape is generally round to oval and ranges in size from five to eight inches long and about equal in diameter. In the United States, the principal fresh market cantaloupe growing regions are California, Arizona and Texas which produce approximately 96,000 acres out of a total annual acreage of more than 113,000 acres (USDA, 1998). Fresh cantaloupes are available in the United States year-round although the greatest supply is from June through October. Fresh cantaloupes are consumed in many forms. They are eaten sliced or diced and used as an ingredient in many prepared foods.

*Cucumis melo* is a member of the family Cucurbitaceae. The Cucurbitaceae is a family of about 90 genera and 700 to 760 species, mostly of the tropics. The family includes pumpkins, squashes, gourds, watermelon, loofah and several weeds. The genus *Cucumis*, to which the cantaloupe, cucumbers, and several melons belong, includes about 70 species. *Cucumis melo* includes a wide range of cultivated plants. Although crosses outside the species are sterile, intraspecific crosses are generally fertile, resulting in a confusing range of variation. The more common cultivated plants fall into four main groups. First are the true cantaloupes of Europe. These have thick, scaly, rough, often deeply grooved, but not netted rinds. Second are the muskmelons, mostly grown in the United States, where they are incorrectly called cantaloupes. These have finely netted rinds with shallow ribs. Third are the casaba or winter melons with large fruits. These have smooth, often yellow rinds. The honeydew melons are in this third group. Fourth are a group of elongated melons of India, China and Japan which are grown as vegetables. Other classification schemes and cultivars could be presented.

Cantaloupe is a simple diploid species with twelve pairs of highly differentiated chromosomes. Large field spaces are required for cantaloupe and the need for labor intensive hand pollination for self as well as cross pollination has resulted in a lag in the knowledge of cantaloupe genetics relative to such crops as tomato. Cantaloupe flowers open after sunrise; the exact time depends on environmental conditions such as sunlight, temperature and humidity. The flower closes permanently in the afternoon of the same day. Almost all pollen is collected and transferred before noon. Typically flowers are staminate although some are also hermaphroditic. Although hermaphroditic flowers are self-fertile, they are incapable of performing self-pollination. Insects are required for pollination. The primary pollinators are bees, particularly honey bees.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

The complexity of inheritance influences choice of the breeding method. Backcross breeding is used to transfer one or a few favorable genes for a heritable trait into a desirable cultivar. This approach has been used extensively for breeding disease-resistant cultivars, nevertheless, it is also suitable for the adjustment and selection of morphological characters, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s) for three years at least. The best lines are candidates for use as parents in new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a focus on clear objectives.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of cantaloupe breeding is to develop new, unique and superior cantaloupe inbred lines and hybrids. The breeder initially selects and crosses two or more parental lines, followed by repeated self pollination or selfing and selection, producing many new genetic combinations. The breeder can theoretically generate billions of different genetic combinations via crossing, selfing and mutations.

Each year, the plant breeder selects the germplasm to advance to the next generation. This germplasm is grown under unique and different geographical, climatic and soil conditions, and further selections are then made, during and at the end of the growing season. The inbred lines developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. This unpredictability results in the expenditure of large research monies to develop a superior new cantaloupe inbred line.

The development of commercial cantaloupe hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable cultivars or inbred line which is the recurrent parent. The source of the trait to be transferred is called the donor parent. After the initial cross, individuals possessing the phenotype of the recurrent parent and the trait of the donor parent are selected and repeatedly, crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Principles of Plant Breeding" John Wiley and Son, pp. 115-161, 1960; Allard, 1960; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny.

Cantaloupe is an important and valuable vegetable crop. Thus, a continuing goal of plant breeders is to develop stable, high yielding cantaloupe hybrids that are agronomically and commercially sound. The reasons for this goal are to maximize the amount of fruits produced on the land used (yield) as well as to improve the fruit agronomic qualities. To accomplish this goal, the cantaloupe breeder must select and develop cantaloupe plants that have the traits that result in superior parental lines that combine to produce superior commercial hybrids.

SUMMARY OF THE INVENTION

According to the invention, there is provided a novel inbred cantaloupe line, designated I446. This invention thus relates to the seeds of inbred cantaloupe line I446, to the plants or parts thereof of inbred cantaloupe line I446, to plants or parts thereof having all the physiological and morphological characteristics of inbred cantaloupe line I446 and to plants or parts thereof having the physiological and morphological characteristics of inbred cantaloupe line I446 listed in Table 1 as determined at the 5% significance level when grown in the same environmental condition. Parts of the inbred cantaloupe plant of the present invention are also provided, such as e.g., pollen obtained from an inbred plant and an ovule of the inbred plant.

In another aspect, the present invention provides regenerable cells for use in tissue culture of inbred cantaloupe plant I446. The tissue culture will preferably be capable of regenerating plants having all the physiological and morphological characteristics of the foregoing inbred cantaloupe plant. Preferably, the cells of such tissue cultures will be embryos, meristematic cells, seeds, callus, pollen, leaves, anthers, roots, root tips, stems, petioles, fruits, cotyledons, hypocotyls, flowers or the like. Protoplasts produced from such tissue culture are also included in the present invention. The cantaloupe plants regenerated from the tissue cultures are also part of the invention.

Also included in this invention are methods for producing a cantaloupe plant produced by crossing the inbred line I446 with itself or another cantaloupe line. When crossed with itself, i.e. crossed with another inbred line I446 plant or self pollinated, the inbred line I446 will be conserved. When crossed with another, different cantaloupe line, an F1 hybrid seed is produced. F1 hybrid seeds and plants produced by growing said hybrid seeds are included in the present invention. A method for producing a F1 hybrid cantaloupe seed comprising crossing inbred line I446 cantaloupe plant with a different cantaloupe plant and harvesting the resultant hybrid cantaloupe seed are also part of the invention. The hybrid cantaloupe seed produced by the method comprising crossing inbred line I446 cantaloupe plant with a different cantaloupe plant and harvesting the resultant hybrid cantaloupe seed are included in the invention, as are included the hybrid cantaloupe plant or parts thereof, seeds included, produced by growing said hybrid cantaloupe seed.

In another embodiment, this invention relates to a method for producing the inbred line I446 from a collection of seeds, collection containing both inbred line I446 seeds and hybrid seeds having I446 as a parental line. Such a collection of seed might be a commercial bag of seeds. Said method comprises planting the collection of seeds. When planted, the collection of seeds will produce inbred line I446 plants from inbred line I446 seeds and hybrid plant from hybrid seeds. The plants having all the physiological and morphological characteristics of cantaloupe inbred line I446 are identified as inbred line I446 parent plants. As previously mentioned, if the inbred line I446 is self pollinated, the inbred line I446 will be preserved, therefore, the next step is controlling pollination of the inbred parent plants in a manner which preserves the homozygosity of said inbred line I446 parent plant, the final step being to harvest the resultant seed.

This invention also relates to methods for producing other inbred cantaloupe lines derived from inbred cantaloupe line I446 and to the inbred cantaloupe lines derived by the use of those methods.

In another aspect, the present invention provides transformed I446 inbred cantaloupe line or parts thereof that have been transformed so that its genetic material contains one or more transgenes, preferably operably linked to one or more regulatory elements. Also, the invention provides methods for producing a cantaloupe plant containing in its genetic material one or more transgenes, preferably operably linked to one or more regulatory elements, by crossing transformed I446 inbred cantaloupe line with either a second plant of another cantaloupe line, or a non transformed cantaloupe plant of the inbred line I446, so that the genetic material of the progeny that results from the cross contains the transgene(s), preferably operably linked to one or more regulatory elements. Transgenic cantaloupe plants, or parts thereof produced by the method are in the scope of the present invention.

More specifically, the invention comprises methods for producing male sterile cantaloupe plants, herbicide resistant cantaloupe plants, insect resistant cantaloupe plants, disease resistant cantaloupe plants, water-stress-tolerant plants, plants with increased sweetness and flavor, plants with increased sugar content, plants with delayed senescence or controlled ripening or plants with improved salt tolerance. Said methods comprise transforming the inbred line I446 cantaloupe plant with nucleic acid molecules that confer male sterility, herbicide resistance, insect resistance, disease resistance, water-stress tolerance, increased sugar content, delayed senescence or controlled ripening or improved salt tolerance, respectively. The transformed cantaloupe plants obtained from the provided methods, including male sterile cantaloupe plant, herbicide resistant cantaloupe plant, insect resistant cantaloupe plant, disease resistant cantaloupe plant, cantaloupe with water stress tolerance, cantaloupe plants with increased sweetness and flavor, cantaloupe plants with increased sugar content, cantaloupe plants with delayed senescence or controlled ripening or cantaloupe plants with improved salt tolerance are included in the present invention. For the present invention and the skilled artisan, disease is understood to be fungal disease, viral disease, bacterial disease or other plant pathogenic diseases and disease resistant plants will encompass plants resistant to fungal, viral, bacterial and other plant pathogens.

In another aspect, the present invention provides for methods of introducing one or more desired trait(s) into the cantaloupe line I446 and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance for bacterial, fungal, or viral disease, male fertility, water-stress tolerance, delayed senescence or controlled ripening, enhanced nutritional quality such as increased sugar content or increased sweetness, enhanced plant quality such as improved drought or salt tolerance, enhanced plant vigor or improve fresh cut application. The gene or genes may be naturally occurring cantaloupe gene(s) or transgene(s) introduced through genetic engineering techniques. The method for introducing the desired trait(s) is preferably a backcrossing process making use of a series of backcrosses to the inbred cantaloupe line I446 during which the desired trait(s) is maintained by selection.

When using a transgene, the trait is generally not incorporated into each newly developed line such as I446 by direct transformation. Rather, the more typical method used by breeders of ordinary skill in the art to incorporate the transgene is to take a line already carrying the transgene and to use such line as a donor line to transfer the transgene into the newly developed line. The same would apply for a naturally occurring trait. The backcross breeding process comprises the following steps: (a) crossing the inbred line I446 plants with plants of another line that comprise the desired trait(s), (b) selecting the F1 progeny plants that have the desired trait(s); (c) crossing the selected F1 progeny plants with the inbred line I446 plants to produce backcross progeny plants; (d) selecting for backcross progeny plants that have the desired trait(s) and physiological and morphological characteristics of cantaloupe inbred line I446 to produce selected backcross progeny plants; and (e) repeating steps (c) and (d) one, two, three, four, five six, seven, eight or more times in succession to produce selected, second, third, fourth, fifth, sixth, seventh, eighth or higher backcross progeny plants that comprise the desired trait(s) and the physiological and morphological characteristics of cantaloupe inbred line I446 as listed in Table 1 and as determined at a 5% significance level when grown in the same environmental conditions. The cantaloupe plants produced by these methods are also part of the invention. Backcrossing breeding methods, well known to one skilled in the art of plant breeding will be further developed in subsequent parts of the specification.

In a preferred embodiment, the present invention provides methods for increasing and producing inbred line I446 seed, whether by crossing a first inbred parent cantaloupe plant with a second inbred parent cantaloupe plant and harvesting the resultant cantaloupe seed, wherein both said first and second inbred cantaloupe plant are the inbred line I446 or by planting an inbred cantaloupe seed of the inbred cantaloupe line I446, growing an inbred line I446 plant from said seed, controlling self-pollination of the plant where the pollen produced by the grown inbred line I446 plant pollinates the ovules produced by the very same inbred line I446 grown plant and harvesting the resultant seed.

The invention further provides methods for developing cantaloupe plants in a cantaloupe plant breeding program using plant breeding techniques including recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, etc.) enhanced selection, genetic marker enhanced selection and transformation. Seeds, cantaloupe plants, and parts thereof produced by such breeding methods are also part of the invention.

Definitions

In the description and tables that follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Cavity. As used herein, cavity refers to the center of the cantaloupe fruit containing seeds and maternal tissues. Cavity measurements are made on a single fruit or recorded as an average of many fruit at harvest maturity and recorded in a convenient unit of measure. Cavity ratings: 1=very poor (non marketable), 3=poor (non marketable), 5=average (marketable) 7=very good (much better than industry standards), 9=superior (further improvement not attainable).

Essentially all the physiological and morphological characteristics. A plant having "essentially all the physiological and morphological characteristics" means a plant having the physiological and morphological characteristics of the recurrent parent, except for the characteristics derived from the converted gene.

Yield. Yield defined as concentrated, semi concentrated or extended. Concentrated=Harvested quantity of yield in x consecutive days of harvest. Semi concentrated=Harvested quantity in x+3-5 consecutive days. Extended=Harvested quantity in x+6-10 days. The Fruit Set may also be defined accordingly to the same criteria, i.e. very concentrated, when the plant sets all of its fruit at nearly the same time; concentrated, when the plant sets all its fruits in a short period of time; semi concentrated, when fruit set is less uniform; and extended, when the plant sets and matures fruit to allow picking over a long period of time.

Firm fruit exterior. Fruit Firmness subjectively tested under field conditions for resistance of fruit exterior against a given pressure. Range is soft, medium, firm and very firm.

Season maturity or maturity. Maturity is considered the date of the onset of harvest and is classified as Very Early, Early, Mid Early, Main and Late or specified by recording the date of the onset of harvest.

Flesh color. Flesh color is defined as degree of intensity of orange. Flesh color ratings 1=very poor (non marketable), 3=poor (non marketable), 5=average (marketable) 7=very good (much better than industry standards), 9=superior (further improvement not attainable).

Netting. The height and density of the netting (reticulation) that covers orange flesh melons. Range is fine, medium, medium coarse and coarse. (i.e.—a fine net would be low and would have noticeable space between the net, a coarse net would be quite high and almost completely cover the fruit exterior. Ideal net is medium or medium coarse. Netting can also be assigned a descriptive number 1=fine net to 10 coarse net.

Number of Boxes per Acre. The Number of Boxes per Acre—6's, 9's, 12's, 15's, 18's or 23's refers to the number of fruit that fit into a standard cantaloupe box.

Quantitative Trait Loci (QTL) Quantitative trait loci refer to genetic loci that control to some degree numerically representable traits that are usually continuously distributed.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Shape. Refers to external fruit shape. Range is Flat Round, Round, round oval, oval, elongate.

Abscission zone. This is the zone of abscission or separation of the fruit from the peduncle at maturity (controlled by ethylene). The resulting zone (or scar) ranges in size, small being preferred over large-range small (<10 mm), medium (10-15 mm), large (15-20 mm), very large (>20 mm)

Blossom scar. This is the remnant scar from the stigmatic surface of the blossom. There is a very broad range in sizes, small is better. Range is small (<10 mm), medium (10-20 mm), large (20-40 mm) and very large (>40 mm).

Fruit size. Western Shipper fruit size determined two ways 1/. Range in kilograms: small (below 1.5), medium (1.5-1.8), large (1.8-2.2), very large (above 2.2) 2/. # Fruit that fit into a standard western melon packing box: 6, 9, 12, 15, 18, 23, 30. Small: some 18's, 23's, 30's, Medium: some 12's, 15's 18's, Large: 9's, 12's, few 15's and Extra Large: few 6's, 9's few 12's.

Soluble Solids. Soluble solids refer to the percent of solid material found in the fruit tissue, the vast majority of which is sugars. Soluble solids are estimated with a refractometer and measured as degrees Brix. Soluble Solids vary with environment. For example, for California summer growing conditions the following range would apply. Very high (>12.5%), high (11.5-12.5%), medium (10.5-11.5%), low <10.5%).

Flesh firmness. Flesh firmness subjectively tested under field conditions for resistance of flesh against a given pressure. Firmness ratings 1=very poor (non marketable), 3=poor (non marketable), 5=average (marketable) 7=very good (much better than industry standards), 9=superior (further improvement not attainable).

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

Collection of seeds. In the context of the present invention a collection of seeds is a grouping of seeds mainly containing similar kind of seeds, for example hybrid seeds having the inbred line of the invention as a parental line, but that may also contain, mixed together with this first kind of seeds, a second, different kind of seeds, of one of the inbred parent lines, for example the inbred line of the present invention. A commercial bag of hybrid seeds having the inbred line of the invention as a parental line and containing also the inbred line seeds of the invention would be, for example such a collection of seeds.

Plant Part. As used herein, the term "plant parts" includes leaves, fruits, stems, roots, seed, embryo, pollen, ovules, flowers, root tips, anthers, tissue, cells and the like.

Plant Cell. Plant cell, as used herein includes plant cells whether isolated, in tissue culture or incorporated in a plant or plant part.

Fruit Weight. The weight of a single fruit or the average of many fruit measured at harvest maturity and recorded in a convenient unit of measure.

Fruit Diameter. The diameter of a single fruit of the average of many fruit measured at harvest maturity and recorded in a convenient unit of measure.

Fruit Length. The length of a single fruit or the average of many fruit measure from stem to blossom end at harvest maturity and recorded in a convenient unit of measure.

Cavity to Diameter ratio. Cavity to Diameter ratio is a measure of the cavity size compared to the overall fruit size of a single fruit or the average of many fruit at harvest maturity and recorded in a convenient unit of measure.

Monecious. the term used to describe a plant variety where each flower exhibits only one sexual character (either male or female) and each plant has flowers of both sexes.

Uniformity. Uniformity, as used herein, describes the similarity between plants or plant characteristics which can be a described by qualitative or quantitative measurements.

Overall Rating. A final or Overall Rating is assigned to variety performance or a varieties characteristic in test or trial situations of a variety. Overall Rating can range from 1=very poor to 10 excellent.

Vine Overall. An overall rating assigned to the performance of a plant's vine. Vine Overall can range from 1=very poor to 10 excellent.

Yield Rating. an overall rating assigned to yield. Yield Rating can range from 1=very poor to 9 excellent.

Oval. Oval is used to describe fruit shape when the length is greater than the width and ranges from a slight oval, oval to heavy oval.

Rind Contrast. A subjective measure of the color difference between the rind and the fruit flesh. 1=no contrast to 10=excellent contrast.

DETAILED DESCRIPTION OF THE INVENTION

Inbred cantaloupe line I446 is a monoecious western shipper cantaloupe with superior characteristics, and provides an excellent parental line in crosses for producing first generation ($F_1$) hybrid cantaloupe. Inbred cantaloupe line I446 is best adapted to southern and southwestern regions of the USA as well as Latin America. Inbred cantaloupe line I446 produces large fruit size with a moderately oval shape, small abscission zone, a medium cavity, medium coarse netting and small blossom scar. The yield is very high, with a concentrated harvest profile. The level of soluble solids is high. The vine is very vigorous with excellent fruit coverage and a very dark green color. Inbred cantaloupe line I446 is also tolerant to races 1 and 2 of *Spaerotheca fuliginea* (Powdery Mildew), races 0 and 2 of *Fusarium* wilt (*Fusarium oxysporum* sp. *melonis*) and is tolerant to sulfur application. Inbred I446 can be used to produce mid early and mid late season maturity hybrid cantaloupe varieties having an semi concentrated yield, with large fruit size having very firm flesh, a slight round oval shape, a firm exterior, a medium net, a very dark orange flesh color and tolerant to races 1 and 2 of *Spaerotheca fuliginea* and to races 0 and 2 of *Fusarium oxysporum*.

Inbred cantaloupe line I446 has superior characteristics and was developed from the accession 47613. F2 seeds of line 47613 were obtained from a planting of a commercial variety (F1) in Altamirano Mexico in March of 1996. The F2 seeds were planted in Harris Moran Research Station in Davis, Calif. in the summer of 1996. The F2 population was segregating broadly for fruit size, fruit shape and sex expression (andromonoecious; monoecious). Three individual F3 selections were made on the basis of fruit size and the monoecious characteristic and were indexed in the fall and winter of 1996/1997 for *Fusarium oxysporum* race 2 and *Sphaerotheca fuliginea* race 2. At this point this line was designated as I446. Good resistance to both pathogens was noted. The three F3 families were planted in May of 1997 in Davis, Calif. where one was chosen to be superior on the basis of uniformity, large fruit size and very deep orange flesh color. These F4 selections were again indexed for disease resistance. The F4 was planted in Davis, Calif. in the summer of 1998, where F5 selections were made. Disease resistance and the majority of horticultural traits were uniform, so the selected F5 progeny were sent to Chile for both advancement to F6 as well as test crossing with key standard male inbreds for evaluation. While F1 testing was being done on hybrids made with I446, further refinement and characterization was done in Davis, Calif. during the summers of 1999, 2000 and 2001 where this lineage became F7, F8, and F9 respectively. Two hybrids using I446 as a female were advanced in the fall of 2000, triggering the first bulk increase of this line. This occurred in Davis, Calif. in the summer of 2002, resulting in lot 02-8073. This lot has been subsequently used to produce stock seed for larger scale productions of hybrid seed. Testing and characterization of I446 has demonstrated highly desirable phenotypes for the following traits: fruit netting, fruit size and shape, external fruit smoothness, internal and external firmness, flavor and aroma, and an extremely deep orange flesh color. The line was also tested for a multitude of other pathogens and stresses, including 3 potyviruses, Cucumber mosaic virus, downy mildew, doradia, aphid tolerance and tolerance to sulfur applications. It has shown moderate resistance to downy mildew and strong tolerance to sulfur applications.

Inbred I446 is similar to the patented cultivar Gdm3. Gdm3 is a full netted western shipping type cantaloupe. While similar to I446, Gdm3 has numerous differences including: I446 matures at least 3-4 days later than Gdm3. GdM3 has a very concentrated harvest period, while I446 has a more extended harvest period. Data indicates that while both lines are moderately oval in shape, GdM3 has a higher length to diameter ratio than I446 and also exhibits more pointed fruit ends. GdM3 has pale to medium orange flesh color, while I446 has a very deep orange flesh color. GdM3 has moderately open net coverage with extensive external fruit mottling, while I446 has a closed full net with only slight to moderate mottling. I446 has stronger tolerance to powdery mildew than GdM3.

During the development of the line, crosses were made to inbred testers for the purpose of estimating the line's general and specific combining ability, and parallel evaluations were run in the USA by the Davis, Calif. Research Station. The inbred was evaluated further as a line and in numerous crosses by Davis, Calif. Research station. The inbred has proven to have exceptional combining ability in hybrid combinations.

The inbred line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred I446.

Inbred cantaloupe line I446 has the following morphologic and other characteristics (based primarily on data collected at Davis, Calif.).

Variety Description Information

PLANT TYPE: *Cucumis melo* var. *reticulatus*
REGION WHERE DEVELOPED: Western US
AREA OF BEST ADAPTATION IN THE USA: Southern California, Arizona
MATURITY: 82 Days
Number of days earlier/later than: 4 days later than Gdm3
LEAF (MATURE BLADE OF THIRD LEAF):
Shape: n/a
Length: 103 mm
Width: 150 mm
Surface: pubescent
FRUIT (at edible maturity):
Length: 19 cm
Diameter: 16.7 cm
Weight: 2460 gm
Shape: moderately oval,
Surface: full netted, no vein tracts,
Blossom scar: small inconspicuous
Ribs: not present
Number of ribs per fruit: n/a
Rib width at medial: n/a
Sutures: n/a
Shipping quality: excellent
Fruit abscise: at maturity with some delays
RIND NET:
Distribution: complete
Coarseness: medium coarse
RIND COLOR (AT EDIBLE MATURITY):
Primary color: green
Net color: grey
Mottling color: buff
Furrow (suture) color: n/a
RIND COLOR (AT FULL MATURITY):
Primary color: buff
Net color: gray
Mottling color: orange
Furrow (suture) color: n/a
FLESH (AT EDIBLE MATURITY):
Color near cavity: deep orange
Color in center: deep orange
Color near rind: deep orange
Refractometer percentage of soluble solids: 9.69%
As compared to Gdm3: 8.33%
Aroma: fruity and slightly floral
Flavor: moderate strong cantaloupe flavor
SEED CAVITY:
Length: 84 mm
Width: 84 mm
Shape in cross-section: triangulate
DISEASE RESISTANCE
Rating (1=susceptible-5=resistant)
Bacterial wilt: 1
Powdery mildew: 4
Watermelon mosaic: 1
Anthracnose: 2
Root rot: 2
*Verticillum* wilt: 2
Downy mildew: 3
Cucumber mosaic: 1
*Fusarium* wilt: 5
Melon rust: 1

FURTHER EMBODIMENTS OF THE INVENTION

This invention also is directed to methods for producing a cantaloupe plant by crossing a first parent cantaloupe plant with a second parent cantaloupe plant wherein either the first or second parent cantaloupe plant is an inbred cantaloupe plant of the line I446. Further, both first and second parent cantaloupe plants can come from the inbred cantaloupe line I446. When self pollinated, or crossed with another inbred line I446 plant, the inbred line I446 will be stable while when crossed with another, different cantaloupe line, an F1 hybrid seed is produced.

An inbred line is produced through several cycles of self-pollination and is considered a homozygous line.

A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting F1 hybrid, theoretically in the arrangement and organization created by the plant breeder in the original parental line.

As long as the homozygosity of the parental lines is maintained, the resulting hybrid cross shall be stable. The F1 hybrid is then a combination of phenotypic characteristics issued from two arrangement and organization of genes, both created by a man skilled in the art through the breeding process.

Still further, this invention also is directed to methods for producing an inbred cantaloupe line I446-derived cantaloupe plant by crossing inbred cantaloupe line I446 with a second cantaloupe plant and growing the progeny seed, and repeating the crossing and growing steps with the inbred cantaloupe line I446-derived plant from 0 to 7 times. Thus, any such methods using the inbred cantaloupe line I446 are part of this invention: selfing, backcrosses, hybrid production, crosses to populations, and the like. All plants produced using inbred cantaloupe line I446 as a parent are within the scope of this invention, including plants derived from inbred cantaloupe line I446. Advantageously, the inbred cantaloupe line is used in crosses with other, different, cantaloupe inbreds to produce first generation ($F_1$) cantaloupe hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which cantaloupe plants can be regenerated, plant calli, plant clumps and plant cells that are intact in plants or parts of plants, such as embryos, meristematic cells, callus, pollen, ovules, flowers, seeds, leaves, roots, root tips, anthers, stems, petioles, fruits, cotyledons and hypocotyls.

As it is well known in the art, tissue culture of cantaloupe can be used for the in vitro regeneration of cantaloupe plants. Tissues cultures of various tissues of cantaloupe and regeneration of plants therefrom are well known and published. By way of example, a tissue culture comprising organs has been used to produce regenerated plants as described in Dirks R., et al. Plant Cell Report 7: 8 626-627 (1989); Homma, Y., et al. Japan J. Breed 41:543-551 (1991). Yoshioka, K., et al. Japan J Breed 42:277-285 (1992); Debeaujon, I., et al. Pl Cell Rep 12:37-40 (1992); Debeaujon, I., et al. Plant Cell Tissue Org Cult 34:91-100 (1993); Fang, G. W., et al. Molecular Plant-Microbe Interactions 6:358-367 (1993); Valles, M. P., et al. Pl Cell Rep 13:145-148 (1994); Ezura, H., et al. Pl Cell Rep 14:107-111 (1994); Kathal, R., et al. Plant Sci 96:137-142 (1994); Adelberg, J. W., et al. Hortscience 29:689-692 (1994). More precisely, in the case of the melon (C. melo), regeneration through organogenesis has been described either directly on cotyledons placed in culture (Dirks, R. et al., Plant Cell Reports, 7:626-627 (1989)), or through the intermediary of calli derived from cotyledons (Mackay, W. et al., Cucurbit Genetics Cooperative, 11:33-34 (1988), Orts, M. et al., Hort Science, 22:666 (1987)), hypocotyls (Abak, K. et al., Cucurbit Genetics Cooperative Report, 3:27-29 (1980), Kathal, R. et al., J. Plant Physiol., 126:59-62 (1986)) or leaves (Kathal, R. et al., Plant Cell Report, 7:449-451 (1988)). The production of melon plants derived from somatic embryos has also been reported, Oridate, T. et al., Japan J. Breeding, 36:424-428 (1986), Branchard, M. et al., C. R. Acad. Sci. Paris, 307, Serie 111:777-780 (1988). Also, De Both et al. in U.S. Pat. No. 6,198,022 teach how to regenerate plants having a normal phenotype from cotyledons. It is clear from the literature that the state of the art is such that these methods of obtaining plants are "conventional" in the sense that they are routinely used and have a very high rate of success. Thus, another aspect of this invention is to provide cells which upon growth and differentiation produce cantaloupe plants having the physiological and morphological characteristics of inbred cantaloupe line I446.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed cantaloupe plants, using transformation methods as described below to incorporate transgenes into the genetic material of the cantaloupe plant(s).

Expression Vectors for Cantaloupe Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Valles et al., Plant Cell Report, 13:3-4 145-148 (1994), Fang et al., Plant Cell Report, 9:3 160-164 (1990). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986). Other selectable marker genes confer resistance to herbicides such as glyphosate, glufosinate or bromoxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS, beta-galactosidase, luciferase and chloramphenicol acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984), Valles et al, Plant Cell Report 3:3-4 145-148 (1994), Shetty et al., Food Biotechnology 11:2 111-128 (1997)

In vivo methods for visualizing GUS activity that do not require destruction of plant tissue are also available. However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain organs, such as leaves, roots, seeds and tissues such as fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in cantaloupe. Optionally, the inducible promoter is operably linked to a nucleotide sequence encoding a signal sequence which is operably linked to a gene for expression in cantaloupe. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., PNAS 90:4567-4571 (1993)); In2 gene from maize which responds to benzenesulfonamide herbicide safeners (Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. U.S.A. 88:0421 (1991)).

B. Constitutive Promoters

A constitutive promoter is operably linked to a gene for expression in cantaloupe or the constitutive promoter is operably linked to a nucleotide sequence encoding a signal sequence which is operably linked to a gene for expression in cantaloupe.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO96/30530.

C. Tissue-Specific or Tissue-Preferred Promoters

A tissue-specific promoter is operably linked to a gene for expression in cantaloupe. Optionally, the tissue-specific promoter is operably linked to a nucleotide sequence encoding a signal sequence which is operably linked to a gene for expression in cantaloupe. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Knox, C., et al., Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., Cell 39:499-509 (1984), Stiefel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is cantaloupe. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., Science 266:789

(1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt alpha-endotoxin gene. Moreover, DNA molecules encoding alpha-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* alpha-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance).

M. A membrane permease, a channel former or a channel blocker. For example, see the disclosure of Jaynes et al., Plant Sci 89:43 (1993), of heterologous expression of a cecropin-beta, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect.

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-alpha-1,4-D-polygalacturonases facilitate fungal colonization and plant nutrient release by solubilizing plant cell wall homo-alpha-1,4-D-galacturonase. See Lamb et al., BioTechnology 10:1436 (1992). The cloning and characterization of a gene which encodes a bean endopolygalacturonase-inhibiting protein is described by Toubart et al., Plant J. 2:367 (1992).

R. A developmental-arrestive protein produced in nature by a plant. For example, Logemann et al., BioTechnology 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvlshikimate-3 posphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., BioTechnology 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2 and Acc1-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Increased sweetness and flavor of the fruit by introduction of a gene encoding sweet-tasting proteins such as monellin (Penarrubia et al., Biotechnology. 1992, 10: 5, 561-564) or thaumatin (Bartoszewski et al, Plant Breeding 122, 347-351 (2003)).

B. Reduced ethylene biosynthesis to control ripening by introduction of an antisense construct of the ACC oxidase into *Cucumis melo*. For example, see Ayub et al, Nature Biotechnology 14: 862 (1996)

C. Delayed senescence and improved ripening control by transferring a gene or acting on the transcription of a gene involved in plant senescence. See Wang et al. in Plant Mol. Bio. 52:1223-1235 (2003) on the role of the deoxyhypusine synthase in the senescence. See also U.S. Pat. No. 6,538,182 issued Mar. 25th, 2003.

D. Improved salt tolerance by transforming *Cucumis melo* plant with HAL 1, a yeast regulatory gene involved in stress tolerance, as shown in Serrano et al., Scientia Horticulturae. 1999, 78: 1/4, 261-269 or in Bordas et al., Transgenic Research. 1997, 6: 1, 41-50.

E. Obtained male sterile plants, especially useful in hybrid melon production, by introduction of a gene encoding a tobacco PR Glucanase as described in tomato (WO9738116) but that can also be used in melon.

Methods for Cantaloupe Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., Science 227:1229 (1985), Jefferson et al., Embo J. 3901-390764, (1987), Valles et al., Pi Cell. Rep. 145-148:13 (1984). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., The Plant Journal 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 micron. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., BioTechnology 6:559-563 (1988), Sanford, J. C., Physiol Plant 7:206 (1990), Klein et al., BioTechnology 10:268 (1992). Gray et al., Plant Cell Tissue and Organ Culture. 1994, 37:2, 179-184.

Another method for physical delivery of DNA to plants is sonication of target cells. Zhang et al., BioTechnology 9:996 (1991). Alternatively, liposome and spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described. D'Halluin et al., Plant Cell 4:1495-1505 (1992) and Spencer et al., Plant Mol. Biol. 24:51-61 (1994).

Following transformation of cantaloupe target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular cantaloupe line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred cantaloupe plant is used in the context of the present invention, this also includes any inbred cantaloupe plant where one or more desired trait has been introduced through backcrossing methods, whether such trait is a naturally occurring one or a transgenic one. Backcrossing methods can be used with the present invention to improve or introduce one or more characteristic into the inbred. The term backcrossing as used herein refers to the repeated crossing of a hybrid progeny back to one of the parental cantaloupe plants for that inbred. The parental cantaloupe plant which contributes the gene or the genes for the desired characteristic is termed the nonrecurrent or donor parent. This terminology refers to the fact that the nonrecurrent parent is used one time in the backcross protocol and therefore does not recur. The parental cantaloupe plant to which the gene or genes from the nonrecurrent parent are transferred is known as the recurrent parent as it is used for several rounds in the backcrossing protocol (Fehr, 1987).

In a typical backcross protocol, the original inbred of interest (recurrent parent) is crossed to a second inbred (nonrecurrent parent) that carries the gene or genes of interest to be transferred. The resulting progeny from this cross are then crossed again to the recurrent parent and the process is repeated until a cantaloupe plant is obtained wherein all the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self pollination and growing of population might be included between two successive backcrosses. Indeed, an appropriate selection in the population produced by the self pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed 1, 2, 3, 4, 5, 6, 7, 8, 9 or more times to parent A to produce selected backcross progeny plants comprising the desired trait of parent B and physiological and morphological characteristics of parent A. Step c) may or may not be repeated and included between the backcrosses of step d.

The selection of a suitable recurrent parent is an important step for a successful backcrossing procedure. The goal of a backcross protocol is to alter or substitute one or more trait(s) or characteristic(s) in the original inbred. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the waxy starch characteristic in corm, require selfing the progeny to determine which plant carry the recessive allele(s).

Many single gene traits have been identified that are not regularly selected for in the development of a new inbred but that can be improved by backcrossing techniques. Single gene traits may or may not be transgenic, i.e. they may be naturally present in the non recurrent parent, examples of these traits include but are not limited to, male sterility (such as a PR glucanase gene or the ms1, ms2, ms3, ms4 or ms5 genes), herbicide resistance (such as bar or PAT genes), gynoecia (such as the g gene), resistance for bacterial, fungal (genes Fom-1 and Fom-2 for resistance to *fusarium* wilt), or viral disease (gene nsv for resistance to melon necrotic spot virus, gene ZYM for the resistance to the zucchini yellow mosaic virus), insect resistance (gene Vat for resistance to *Aphis gossypii*), male fertility, enhanced nutritional quality, enhanced sugar content, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc, "Principles of Plant Breeding). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a variety with exactly the adaptation, yielding ability and quality characteristics of the recurrent parent but superior to that parent in the particular characteristic(s) for which the improvement program was undertaken. Therefore, this method provides the plant breeder with a high degree of genetic control of his work.

The method is scientifically exact because the morphological and agricultural features of the improved variety could be described in advance and because the same variety could, if it were desired, be bred a second time by retracing the same steps (Briggs, "Breeding wheats resistant to bunt by the backcross method", 1930 Jour. Amer. Soc. Agron., 22: 289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred.

The backcross technique is not only desirable when breeding for disease resistance but also for the adjustment of morphological characters, colour characteristics and simply inherited quantitative characters such as earliness, plant height and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e. grain size. 'Lady Wright', a long grain variety was used as the donor parent and 'Coloro', a short grain one as the recurrent parent. After four backcrosses, the medium grain type variety 'Calady' was produced.

TABLES

In the tables that follow, the traits and characteristics of inbred cantaloupe I446 are given compared to other inbreds. The data collected are presented for key characteristics and traits. Inbred I446 was tested as an inbred, but also in several hybrid combinations at numerous locations, with two or three replications per location. Information about these inbreds and hybrids, as compared to several check inbred and hybrids is presented.

Table 2 below shows the characteristics of inbred I446 as compared to inbred Gdm3. Column 1 shows fruit number, column 2 shows fruit weight in kg, column 3 shows soluble solids content in brix, column 4 shows fruit diameter in cm, column 5 shows fruit length in centimetres, column 6 shows cavity size in cm, and column 7 shows the cavity to diameter ratio in cm.

TABLE 2

Characteristics of inbred I446 as compared to inbred Gdm3

| Fruit | Fruit weight | | Soluble Solids | | Fruit Diameter | | Fruit Length | | Cavity (cm) | | Cavity to Diameter ratio | |
|---|---|---|---|---|---|---|---|---|---|---|---|---|
| | I446 | Gdm3 | I446 | Gdm3 | I446 | Gdm3 | I446 | Gdm3 | I446 | Gdm3 | I446 | Gdm3 |
| 1 | 2.17 | 2.82 | 7 | 9.6 | 15.9 | 18.3 | 19.2 | 19.4 | 7.9 | 9 | 0.5 | 0.49 |
| 2 | 2.67 | 2.53 | 11.4 | 8.4 | 17.1 | 18.4 | 20 | 17.6 | 9.4 | 9.6 | 0.55 | 0.52 |

TABLE 2-continued

Characteristics of inbred I446 as compared to inbred Gdm3

| Fruit | Fruit weight I446 | Fruit weight Gdm3 | Soluble Solids I446 | Soluble Solids Gdm3 | Fruit Diameter I446 | Fruit Diameter Gdm3 | Fruit Length I446 | Fruit Length Gdm3 | Cavity (cm) I446 | Cavity (cm) Gdm3 | Cavity to Diameter ratio I446 | Cavity to Diameter ratio Gdm3 |
|---|---|---|---|---|---|---|---|---|---|---|---|---|
| 3 | 2.53 | 2.22 | 11.2 | 9 | 17.3 | 16.5 | 19.7 | 16.1 | 8.6 | 8.6 | 0.5 | 0.52 |
| 4 | 2.13 | 2.02 | 11 | 8.8 | 16 | 15.2 | 19.1 | 17.9 | 8.3 | 6.7 | 0.52 | 0.44 |
| 5 | 2.56 | 2.06 | 11.2 | 6 | 17 | 15.9 | 20.6 | 15.8 | 8.9 | 7.6 | 0.52 | 0.48 |
| 6 | 2.94 | 2.69 | 10.6 | 8.4 | 17.5 | 17.3 | 20.5 | 18.9 | 9.4 | 8.5 | 0.54 | 0.49 |
| 7 | 2.92 | 1.78 | 11 | 8.6 | 17.9 | 15.5 | 19.8 | 15.5 | 9.2 | 7.1 | 0.51 | 0.46 |
| 8 | 2.1 | 2.43 | 8.6 | 9.6 | 16.1 | 16.5 | 17.4 | 18.3 | 8.2 | 7.4 | 0.51 | 0.45 |
| 9 | 2.58 | 1.9 | 11.6 | 7.2 | 17.5 | 15.1 | 19.5 | 15.1 | 8.7 | 7.6 | 0.5 | 0.5 |
| 10 | 2.22 | 2.42 | 9.6 | 9 | 15.7 | 16.4 | 19.3 | 17.4 | 8 | 8.2 | 0.51 | 0.5 |
| 11 | 2.29 | 1.56 | 11 | 8.2 | 16.5 | 14.1 | 19.2 | 14.6 | 10 | 6 | 0.61 | 0.43 |
| 12 | 2.92 | 1.91 | 10 | 6.4 | 18.3 | 15.2 | 19.4 | 15.5 | 9.1 | 6.7 | 0.5 | 0.44 |
| 13 | 2.54 | 1.6 | 8.8 | 9 | 16.8 | 14.6 | 18.7 | 14.9 | 8.5 | 6.7 | 0.51 | 0.46 |
| 14 | 2.51 | 1.3 | 9 | 8.2 | 17.4 | 13.3 | 18.4 | 14.5 | 9 | 6.7 | 0.52 | 0.5 |
| 15 | 2.33 | 1.99 | 6.6 | 10.2 | 16.8 | 16 | 19 | 16.3 | 8.6 | 7.2 | 0.51 | 0.45 |
| 16 | 2.72 | 1.78 | 10.2 | 10.6 | 17.4 | 14.6 | 20.4 | 16.2 | 8.8 | 6.1 | 0.51 | 0.42 |
| 17 | 1.74 | 1.11 | 10.6 | 6.6 | 14.8 | 12.8 | 17.2 | 13.2 | 8.2 | 5.7 | 0.55 | 0.46 |
| 18 | 2.69 | 1.82 | 11.4 | 7.4 | 17 | 15.1 | 19.8 | 16.4 | 8.2 | 6.6 | 0.48 | 0.44 |
| 19 | 2.43 | 1.26 | 8.8 | 8 | 16.4 | 13 | 19.3 | 14.9 | 8.6 | 5.3 | 0.52 | 0.41 |
| 20 | 2.94 | 1.19 | 12.2 | 6 | 16.9 | 13.2 | 20 | 14.2 | 6.8 | 6.7 | 0.4 | 0.51 |
| 21 | 2.27 | 1.07 | 10 | 6 | 16.1 | 12.7 | 18.6 | 12.7 | 8.7 | 5.6 | 0.54 | 0.44 |
| 22 | 2.26 | 1.98 | 8 | 8 | 16.7 | 15.7 | 18 | 18.9 | 7.8 | 7 | 0.47 | 0.45 |
| 23 | 2.38 | 3.06 | 9 | 12.6 | 16.8 | 17.8 | 17.8 | 19.4 | 8.2 | 8.1 | 0.49 | 0.46 |
| 24 | 2.42 | 1.85 | 8.8 | 11 | 16.4 | 15.3 | 19.5 | 16.2 | 7.6 | 7.2 | 0.46 | 0.47 |
| 25 | 2.37 | 1.84 | 9 | 8.6 | 16.8 | 14.8 | 18.2 | 15.4 | 8.2 | 6 | 0.49 | 0.41 |
| 26 | 2.5 | 2.13 | 9.8 | 9.4 | 17 | 15.8 | 18.8 | 18.6 | 7.7 | 7 | 0.45 | 0.44 |
| 27 | 1.52 | 1.33 | 6 | 6.6 | 14.2 | 13.3 | 15.4 | 14.6 | 7.8 | 5.9 | 0.55 | 0.44 |
| 28 | 2.45 | 1.5 | 9 | 8 | 17 | 14 | 18 | 14.5 | 7.6 | 6.3 | 0.45 | 0.45 |
| 29 | 2.74 | 1.33 | 10 | 8 | 17.3 | 13.3 | 18.6 | 14.5 | 8.1 | 5.7 | 0.47 | 0.43 |
| 30 | 3.09 | 1.18 | 9.4 | 6.6 | 17.8 | 13.1 | 20.5 | 14.1 | 8.6 | 6.8 | 0.48 | 0.52 |
| Mean | 2.46 | 1.86 | 9.69 | 8.33 | 16.75 | 15.09 | 19 | 16.05 | 8.42 | 6.99 | 0.5 | 0.46 |

Table 3 below shows the characteristics of hybrid I446*I407 containing a parental line as compared to Hybrid HMX 7605 containing Gdm3 as a line. Column 1 shows fruit number, column 2 shows fruit weight in kg, column soluble solids content in brix, column 4 shows fruit diameter in cm, and column fruit length in cm.

TABLE 3

Characteristics of hybrid I446*I407 containing I446 as a parental line as compared to Hybrid HMX 7605 containing Gdm3 as a parental line

| Fruit | Fruit weight I446*I407 | Fruit weight HMX 7605 | Soluble Solids I446*I407 | Soluble Solids HMX 7605 | Fruit Diameter I446*I407 | Fruit Diameter HMX 7605 | Fruit Length I446*I407 | Fruit Length HMX 7605 |
|---|---|---|---|---|---|---|---|---|
| 1 | 4.56 | 2.79 | 10 | 8.2 | 22.1 | 16.9 | 25.5 | 19.8 |
| 2 | 2.53 | 1.53 | 11 | 6.2 | 17.1 | 13.8 | 18.4 | 15.6 |
| 3 | 3.48 | 3.37 | 11.2 | 6.4 | 19.6 | 18.5 | 20.3 | 20.5 |
| 4 | 3.24 | 2.42 | 10.4 | 8.8 | 19 | 16.4 | 19.2 | 18.4 |
| 5 | 3.63 | 2.4 | 13.6 | 11 | 18.5 | 16.3 | 20.7 | 17.7 |
| 6 | 2.37 | 2.54 | 9.2 | 11.6 | 16.3 | 17.7 | 18.2 | 18.9 |
| 7 | 2.75 | 2 | 11.4 | 9.6 | 18.4 | 16 | 17.4 | 15.5 |
| 8 | 2.8 | 2.88 | 9.2 | 13 | 17.8 | 18.2 | 18.2 | 19.2 |
| 9 | 3.09 | 2.27 | 12.6 | 8.6 | 18 | 16.1 | 20.6 | 17 |
| 10 | 2.2 | 3.45 | 6 | 8.2 | 16.5 | 18.5 | 16.5 | 20.4 |
| 11 | 2.3 | 2.34 | 8.6 | 9.4 | 16.5 | 17.7 | 17 | 18 |
| 12 | 3.02 | 3.09 | 9.6 | 11 | 18.4 | 18.2 | 18.3 | 19.5 |
| 13 | 2.72 | 3.38 | 6 | 10.4 | 18 | 19.2 | 19 | 19.7 |
| 14 | 2.79 | 3.81 | 10.6 | 10.8 | 17.9 | 18.8 | 19.4 | 23.2 |
| 15 | 2.32 | 3.48 | 11.4 | 11.8 | 16.5 | 17.9 | 17.7 | 21 |
| 16 | 2.66 | 3.16 | 7.2 | 13 | 17.7 | 18.1 | 17.2 | 19.3 |
| 17 | 1.42 | 1.52 | 8.6 | 9 | 14.4 | 15 | 14.9 | 14.5 |
| 18 | 2.8 | 2.88 | 6.8 | 11.4 | 18.3 | 18.5 | 18.6 | 18.6 |
| 19 | 2.64 | 3.57 | 11 | 9 | 16.7 | 19 | 19.8 | 21.7 |
| 20 | 1.87 | 2.45 | 9.8 | 7.2 | 15.4 | 15.9 | 16.9 | 18.8 |
| 21 | 3.1 | 3.23 | 10.4 | 12 | 18.1 | 18.8 | 19.7 | 20.2 |
| 22 | 2.13 | 2.6 | 8.4 | 11 | 16 | 16.3 | 17.9 | 20.1 |
| 23 | 2.44 | 2.26 | 9 | 9.8 | 16.6 | 15.8 | 18.4 | 18.5 |
| 24 | 1.71 | 2.14 | 11 | 12.6 | 14.8 | 15.6 | 16.7 | 18.6 |
| 25 | 1.37 | 2.29 | 7.2 | 9 | 13.7 | 16.1 | 14.7 | 19.3 |

TABLE 3-continued

Characteristics of hybrid I446*I407 containing I446 as a parental line as compared to Hybrid HMX 7605 containing Gdm3 as a parental line

|  | Fruit weight | | Soluble Solids | | Fruit Diameter | | Fruit Length | |
|---|---|---|---|---|---|---|---|---|
| Fruit | I446*I407 | HMX 7605 | I446*I407 | HMX 7605 | I446*I407 | HMX 7605 | I446*I407 | HMX 7605 |
| 26 | 2.72 | 2.41 | 10.2 | 11 | 18.5 | 16.8 | 16.6 | 17.7 |
| 27 | 2.55 | 2.59 | 8 | 10.6 | 16.8 | 16.5 | 19.2 | 19.5 |
| 28 | 1.95 | 1.8 | 7 | 7 | 15.9 | 14.8 | 16.7 | 16.6 |
| 29 | 2.63 | 1.74 | 12 | 9 | 17.8 | 14.8 | 18.5 | 16.6 |
| 30 | 2.11 | 2.34 | 9.6 | 8 | 16.1 | 16 | 16.6 | 18.8 |
| Mean | 2.60 | 2.62 | 9.57 | 9.82 | 17.25 | 16.94 | 18.29 | 18.77 |

Table 4 below shows characteristics of hybrids I446*I444 and I446*I407 containing I446 as a parental line as compared to hybrids containing Gdm3 as a parental line. Column 1 shows the hybrid name, column 2 shows the trial year and location, column 3 shows plant uniformity (1=not uniform to 10=very uniform), Column 4 shows overall rating (1=very poor to 10=excellent), column 5 shows overall rating for the vine (1=very poor to 10=excellent), column 6 shows the yield rating (1=very poor (non marketable), 3=poor (non marketable), 5=average (marketable) 7=very good (much better than industry standards), 9=superior (further improvement not attainable)), column 7 shows concentration of fruit set, column 8 shows maturity, and column 9 shows fruit shape.

Table 5 below shows characteristics of hybrids I446*I444 and I446*I407 containing I446 as a parental line as compared to hybrids containing Gdm3 as a parental line. Column 1 shows the hybrid name, column 2 shows the trial year and location, column 3 shows the net type, column 4 shows firmness ratings, column 5 shows fruit color ratings, column 6 shows rind contrast, column 7 shows thickness of the rind where thickness ranges from 1=very thin (not marketable) to 10=very thick (marketable), and column 8 shows cavity size.

TABLE 4

Characteristics of hybrids I446*I444 and I446*I407 containing I446 as a parental line compared to hybrids containing Gdm3 as a parental line

| VARIETY | YEAR/AREA | UNIFORMITY | OVERALL RATING | VINE OVERALL | YIELD RATING | FRUIT SET | MATURITY | SHAPE |
|---|---|---|---|---|---|---|---|---|
| HMX7605 | 2000/PM | 5.5 | 5 | 5 | 4.5 | CONCENTRATED | VERY EARLY | OVAL |
| HMX7605 | 2000/PM | 6 | 8 | 5.5 | 6 | CONCENTRATED | VERY EARLY | OVAL |
| HYMARK | 2000/PM | 6 | 5.5 | 6.5 | 5.5 | SEMI CONCENTRATED | MIDE EALY-MAIN | ROUND |
| I446*I444 | 2000/PM | 5 | 5.5 | 5 | 5 | SEMI CONCENTRATED | MID EARLY | ROUND/OVAL |
| I446*I407 | 2000/PM | 5.5 | 6 | 6 | 6.5 | SEMI CONCENTRATED | MID EARLY | SLIGHT OVAL |
| I446*I407 | 2000/YUMA | 5.5 | 6 | 5 | 6 | SEMI CONCENTRATED | EARLY | SLIGHT OVAL/OVAL |
| I446*I444 | 2000/YUMA | 7.5 | 6 | 5 | 5.5 | SEMI CONCENTRATED | MID-EARLY | SLIGHT OVAL |
| HMX7605 | 2000/YUMA | 6 | 6 | 6 | 6 | VERY CONCENTRATED | EARLY | ROUND/SLIGHT OVAL |
| I446*I407 | 2001/DAVIS | 6.5 | 6.5 | 6 | 6 | SEMI CONCENTRATED | MID-EARLY | SLIGHT-MODEARATE OVAL |
| I446*I444 | 2001/DAVIS | 6 | 6 |  | 7.5 | SEMI CONCENTRATED |  | SLIGHT OVAL |
| HMX7605 | 2001/DAVIS | 6 | 5.5 | 5.5 | 6 | VERY CONCENTRATED | EARLY | MODERATE-HEAVY OVAL |
| I446*I407 | 2001/IMJG |  |  | 7 | 5 | SEMI CONCENTRATED | MAIN | ROUNDTO OVAL |
| I446*I407 | 2002/FLORIDA |  | 7 | 5.5 |  | CONCENTRATED | EARLY | SLIGHT OVAL |
| I446*I444 | 2002/FLORIDA | 6 | 6 | 5 |  | CONCENTRATED | VERY EARLY | ROUND |
| HYMARK | 2002/FLORIDA |  | 5.5 | 5 |  | SEMI CONCENTRATED | MID-EARLY | SLIGHT OVAL |
| HMX7605 | 2002/FLORIDA |  | 5.5 | 5 |  | CONCENTRATED | EARLY | SLIGHT OVAL |

TABLE 5

Characteristics of hybrids I446*I444 and I446*I407 containing I446 as a parental line as compared to hybrids containing Gdm3 as a parental line

| VARIETY | YEAR/AREA | NETTING | FIRMNESS | COLOR | RIND CONTRAST | THICKNESS | CAVITY SIZE |
|---|---|---|---|---|---|---|---|
| HMX7605 | 2000/PM | 5 | 6 | 5 | 5.5 | 5.5 | 5.5 |
| HMX7605 | 2000/PM | 5 | 6 | 5.5 | 5.5 | 6 | 6 |
| HYMARK | 2000/PM | 5.5 | 6 | 7 | 6 | 6 | 5.5 |
| I446*I444 | 2000/PM | 6 | 7 | 7 | 5.5 | 5.5 | 5 |
| I446*I407 | 2000/PM | 6 | 7 | 6.5 | 6 | 5 | 4 |
| I446*I407 | 2000/YUMA | 6 | 7 | 6 | 5 | 5.5 | 5.5 |
| I446*I444 | 2000/YUMA | 6 | 6 | 7 | 7 | 6.5 | 6 |
| HMX7605 | 2000/YUMA | 6.5 | 7 | 5.5 | 6 | 5.5 | 4 |
| I446*I407 | 2001/DAVIS | 6.5 | 7.5 | 6.5 | 6.5 | 6 | 4.5 |
| I446*I444 | 2001/DAVIS | 6.5 | 7 | 5.5 | 5.5 | 6 | 5.5 |
| HMX7605 | 2001/DAVIS | 5.5 | 6 | 6 | 6 | 5.5 | 4 |
| HYMARK | 2001/DAVIS |  | 6.5 | 6.5 | 6.5 | 5 | 6 |
| I446*I407 | 2001/IMJG | 7 | 7 | 7 | 7 | 7 | 5 |
| I446*I407 | 2002/FLORIDA | 7.5 |  |  |  |  |  |
| I446*I444 | 2002/FLORIDA | 6 |  |  |  |  |  |
| HYMARK | 2002/FLORIDA | 5 |  |  |  |  |  |
| HMX7605 | 2002/FLORIDA | 5 |  |  |  |  |  |

Table 6 below shows characteristics of hybrids I446*I444 and I446*I407 containing I446 as a parental line as compared to hybrids containing Gdm3 as a parental line. Column 1 shows the hybrid name, column 2 shows the trial year and location, columns 3-7 show fruit size, and columns 8-10 show soluble solids content in brix. For fruit size, an X indicates that size was present at harvest, an XX indicates many fruit were present in that size class at harvest and an F indicates one or a relatively few fruit of that size class were present

TABLE 6

Characteristics of hybrids I446*I444 and I446*I407 containing I446 as a parental line as compared to hybrids containing Gdm3 as a parental line

| VARIETY | YEAR/AREA | SIZE-6 | SIZE-9 | SIZE-12 | SIZE-15 | SIZE-18 | BRIX-1 | BRIX-2 | BRIX-3 |
|---|---|---|---|---|---|---|---|---|---|
| HMX7605 | 2000/PM |  | X | X | X |  | 11.6 |  |  |
| HMX7605 | 2000/PM |  | X | X | X |  | 10.5 | 12.2 | 11.5 |
| HYMARK | 2000/PM |  |  | F | X |  | 12 |  |  |
| I446*I444 | 2000/PM |  | X | X | X |  | 11.8 |  |  |
| I446*I407 | 2000/PM |  | X | X | F |  | 10.2 | 8.4 |  |
| I446*I407 | 2000/YUMA |  | X | X |  |  | 12.2 | 10.2 |  |
| I446*I444 | 2000/YUMA |  |  | X | X |  | 11.4 | 13.8 |  |
| HMX7605 | 2000/YUMA |  | X |  |  |  | 11.5 | 13.4 |  |
| I446*I407 | 2001/DAVIS |  | X | X | F |  | 13 | 13.6 | 11 |
| I446*I444 | 2001/DAVIS |  | F | XX | X |  | 10.4 |  |  |
| HMX7605 | 2001/DAVIS | F | X | F |  |  | 14.2 | 12 |  |
| HYMARK | 2001/DAVIS |  |  |  |  |  | 10.4 |  |  |
| I446*I407 | 2001/IMJG |  |  |  | X |  |  |  |  |
| I446*I407 | 2002/FLORIDA |  | XX | X |  |  |  |  |  |
| I446*I444 | 2002/FLORIDA |  | X | XX |  |  |  |  |  |
| HYMARK | 2002/FLORIDA |  |  | X | XX | F |  |  |  |
| HMX7605 | 2002/FLORIDA | F | XX |  |  |  |  |  |  |

Table 7 below shows characteristics of hybrids containing I446 as a parental line. Column 1 shows the hybrid name, column 2 shows trial year and location, column 3 shows overall rating, column 4 shows yield rating, column 5 shows yield concentration, column 6 shows maturity, column 7 shows netting, column 8 shows firmness rating, column 9 shows fruit shape, and columns 10-12 show soluble solids content in brix.

TABLE 7

| Hybrid | Location | Overall Rating | Yield Rating | Yield | Maturity | Netting | Firmness | Shape | Brix_1 | Brix_2 | Brix_3 |
|---|---|---|---|---|---|---|---|---|---|---|---|
| HMX 4587 | Delaware | | | | | 6 | 5 | Moderately Oval | 8.60 | 8.00 | |
| HMX 4587 | North Carolina | | 5 | | | 6 | | Moderately Oval | 6.40 | 8.60 | |
| HMX 4587 | Davis | | 8 | Concentrate | Mid Early | 6 | 6 | Round to Slightly Oval | 12.00 | | |
| HMX 4597 | Yuma | 6 | 8 | Semi concentrate | Early | 7 | 5 | Round | 12.20 | | |
| HMX 4597 | Mexico Torreon | 5 | 4 | | Early | | 5 | | 6.00 | | |
| HMX 4597 | Davis | | 6 | Concentrate | Early | 6 | | Round to Slightly Oval | | | |
| HMX 4597 | California North | 8 | 8 | Extended | Main | 6 | 6 | Round to Slightly Oval | 10.40 | 13.00 | |
| HMX 4598 | Yuma | | 8 | Concentrate | Mid Early | 7 | 7 | | 14.00 | | |
| HMX 4598 | Mexico Torreon | 5 | | Extended | Early | 7 | 6 | | 9.00 | 8.90 | 10.00 |
| HMX 4598 | Davis | 6 | 7 | Concentrate | | 6 | | Moderately Oval | | | |
| HMX 5589 | Yuma | 8 | 8 | Concentrate | Mid Early | 6 | 7 | Round to Slightly Oval | | | |
| HMX 5589 | Mexico Torreon | 6 | 7 | Concentrate | Early | 7 | 7 | | 6.20 | 9.00 | 12.40 |
| HMX 5589 | California North | | 8 | Semi concentrate | Early | 6 | | Round to Slightly Oval | 11.00 | 11.00 | |
| MXP 6023 | Yuma | 8 | 7 | | Very Early | 6 | 8 | | 13.10 | 13.10 | |
| MXP 6401 | Yuma | 8 | 7 | Concentrate | Mid Early | 6 | | | 14.80 | 13.10 | |
| MXP 6506 | Yuma | 6 | | | | 6 | | Round to Slightly Oval | | | |
| MXP 6578 | Yuma | 7 | 7 | | Mid Early | | 6 | | | | |
| MXP 6597 | Yuma | | 8 | Semi concentrate | Late | | | | | | |
| MXP 6604 | Yuma | | 8 | 7 | Concentrate | Main | 5 | | Round to Slightly Oval | | | |
| MXP 6615 | Yuma | | 7 | Semi concentrate | | 6 | 7 | Round to Slightly Oval | 14.20 | 14.40 | |
| MXP 6626 | Davis | | 8 | Semi concentrate | Main | | 7 | Round to Slightly Oval | 15.80 | 14.00 | |
| MXP 6710 | Yuma | | 8 | Semi concentrate | Early | 7 | 6 | Round to Slightly Oval | 14.80 | 15.60 | |
| MXP 6716 | Yuma | 8 | 8 | Concentrate | Main | 7 | 5 | Moderately Oval | 14.00 | 14.50 | |
| MXP 6725 | Yuma | | 7 | Concentrate | Mid Early | 7 | 6 | Round to Slightly Oval | 13.14 | 14.00 | |
| MXP 6725 | Mexico Torreon | 6 | 5 | | Mid Early | 7 | 7 | Round to Slightly Oval | 14.20 | 11.20 | |
| MXP 6785 | Davis | 7 | 8 | Concentrate | Early | 6 | 7 | Round to Slightly Oval | 12.80 | | |
| MXP 6843 | Yuma | 8 | 6 | Concentrate | Early | 7 | 7 | Round to Slightly Oval | 12.80 | 12.90 | |
| MXP 6855 | Davis | | 8 | Semi concentrate | Mid Early | 5 | 7 | Moderately Oval | | | |
| MXP 6862 | Davis | | 7 | Concentrate | Early | 6 | | Moderately Oval | 13.50 | | |
| MXP 6869 | Davis | 6 | 7 | Concentrate | Early | | 7 | Moderately Oval | 11.80 | | |
| MXP 6882 | Davis | 7 | 8 | Semi concentrate | Main | 5 | | Round to Slightly Oval | 13.50 | | |
| MXP 6932 | Yuma | 8 | 7 | Concentrate | Late | 7 | | Moderately Oval | | | |
| MXP 6974 | Yuma | | 8 | Concentrate | Very Early | 7 | 6 | Round to Slightly Oval | 12.20 | 12.20 | |
| MXP 6986 | Yuma | 8 | | Semi concentrate | Mid Early | 6 | 5 | Round to Slightly Oval | 13.40 | 13.40 | |
| MXP 7022 | Davis | 7 | 7 | Extended | Late | 6 | | Round to Slightly Oval | | | |
| MXP 7028 | Davis | 7 | 7 | Concentrate | Early | 6 | | Round to Slightly Oval | | | |
| MXP 7037 | Davis | 6 | 7 | | | 7 | | Moderately Oval | | | |
| MXP 7047 | Davis | 7 | 8 | Concentrate | Mid Early | 6 | | Round to Slightly Oval | | | |
| MXP 7073 | Davis | | 7 | Concentrate | Early | 6 | | Round to Slightly Oval | | | |
| MXP 7172 | Davis | 6 | 7 | | Main | | | Moderately Oval | 12.00 | | |

DEPOSIT INFORMATION

A deposit of the Harris Moran Seed Company proprietary inbred cantaloupe line I446, hybrid cantaloupe 1446*1444 and hybrid cantaloupe 1446*1407 disclosed above and recited in the appended claims has been made with the National Collections of Industrial Food and Marine Bacteria (NCIMB), Ferguson Building, Craibstone Estate, Bucksburn, Aberdeen AB21 9YA, Scotland, United Kingdom. The data of deposit for inbred cantaloupe line 1446 was Aug. 10, 2006. The date of deposit for hybrid cantaloupe 1446*1444 and hybrid cantaloupe 14461407 was Aug. 30, 2006. The deposits of 2,500 seeds was taken from the same deposit maintained by Harris Moran Seed Company since prior to the filing date of this application. All restrictions upon the deposits have been removed, and the deposits are intended to meet all of the requirements of 37 C.F.R. §1.801-1.809. The NCIMB accession number for inbred cantaloupe line 1446 is NCIMB 41427. The NCIMB accession number for hybrid cantaloupe 1446*1444 is NCIMB 41434. The NCIMB accession number for hybrid cantaloupe 1446*1407 is NCIMB 41435. The deposits will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. A seed of cantaloupe inbred line I446, wherein a representative sample of seed of said line was deposited under NCIMB No. 41427.

2. A cantaloupe plant, or a part thereof, produced by growing the seed of claim 1.

3. A cantaloupe plant, or a part thereof, having all of the physiological and morphological characteristics of inbred line I446.

4. A tissue culture of cells produced from the plant of claim 2, wherein the cells are produced from a plant part selected from the group consisting of protoplasts, embryos, meristematic cells, callus, pollen, ovules, flowers, seeds, leaves, roots, root tips, anthers, stems, petioles, fruits, cotyledons and hypocotyls.

5. A cantaloupe plant regenerated from the tissue culture of claim 4, wherein the regenerated plant has all of the morphological and physiological characteristics of inbred line I446.

6. A method for producing a hybrid cantaloupe seed wherein the method comprises crossing the plant of claim 2 with a different cantaloupe plant and harvesting the resultant hybrid cantaloupe seed.

7. A method for producing a cantaloupe plant that contains in its genetic material one or more transgenes, wherein the method comprises crossing the cantaloupe plant of claim 2 with either a second plant of another cantaloupe cultivar which contains a transgene or a transformed cantaloupe plant of the cantaloupe inbred line I446, so that the genetic material of the progeny that result from the cross contains the transgene(s) operably linked to a regulatory element.

8. A method of introducing a desired trait into cantaloupe inbred line I446 wherein the method comprises:

(a) crossing the inbred line I446 plants grown from the inbred line I446 seed, wherein a representative sample of seed of said line was deposited under NCIMB No. 41427, with plants of another cantaloupe line that comprise a desired trait to produce F1 progeny plants, wherein the desired trait is selected from the group consisting of male sterility, male fertility, herbicide resistance, insect resistance, disease resistance, increased sugar content, increased sweetness, increased flavor, improved ripening control and improved salt tolerance;

(b) selecting one or more progeny plants that have the desired trait to produce selected progeny plants;

(c) crossing the selected progeny plants with the inbred line I446 plants to produce backcross progeny plants;

(d) selecting for backcross progeny plants that have the desired trait and physiological and morphological characteristics of cantaloupe inbred line I446 listed in Table 1 to produce selected backcross progeny plants; and (e) repeating steps (c) and (d) three or more times in succession to produce selected fourth or higher backcross progeny plants that comprise the desired trait and all of the physiological and morphological characteristics of cantaloupe inbred line I446 as listed in the VARIETY DESCRIPTION INFORMATION.

9. A cantaloupe plant produced by the method of claim 8, wherein the plant has the desired trait and all of the physiological and morphological characteristics of cantaloupe inbred line I446 listed in the VARIETY DESCRIPTION INFORMATION.

10. A hybrid cantaloupe seed designated I446* I444 having inbred line I446 as a parental line, wherein a representative sample of seed was deposited under NCIMB No. 41434, and hybrid cantaloupe seed designated I446*I407 having inbred line I446 as a parental line, wherein a representative sample of seed was deposited under NCIMB No. 41435.

11. A cantaloupe plant produced by growing the cantaloupe seed of claim 10.

12. A method for producing inbred line I446, wherein a representative sample of seed of said line was deposited under NCIMB No. 41427, wherein the method comprises:

a) planting a collection of seed comprising seed of a hybrid, one of whose parents is inbred line I446, said collection also comprising seed of said inbred;

b) growing plants from said collection of seed;

c) identifying the plants having the physiological and morphological characteristics of cantaloupe inbred line I446 as inbred parent plants;

d) controlling pollination of said inbred parent plants in a manner which preserves the homozygosity of said inbred parent plant; and e) harvesting the resultant seed.

13. A method for producing inbred line I446 seed, wherein a representative sample of seed of said line was deposited under NCIMB No. 41427, wherein the method comprises crossing a first inbred parent cantaloupe plant with a second inbred parent cantaloupe plant and harvesting the resultant cantaloupe seed, wherein both said first and second inbred cantaloupe plant are the cantaloupe plant of claim 3.

14. A method for producing inbred line I446 seed, wherein a representative sample of seed of said line was deposited under NCIMB No. 41427, wherein the method comprises:

a) planting an inbred cantaloupe seed of claim 1;
b) growing a plant from said seed;
c) controlling pollination in a manner that the pollen produced by the grown plant pollinates the ovules produced by the grown plant; and
d) harvesting the resultant seed.

15. A method for producing a cantaloupe plant comprising transforming the cantaloupe plant of claim 2 with a transgene conferring a trait selected from the group consisting of herbicide resistance, insect resistance, disease resistance, increased sweetness, improved ripening control and improved salt tolerance.

16. A cantaloupe plant produced by the method of claim 15 having one or more traits selected from the group consisting of herbicide resistance, insect resistance and disease resistance.

17. A cantaloupe plant produced by the method of claim 15 having one or more traits selected from the group consisting of increased sweetness, improved ripening control and improved salt tolerance.

18. A method for producing a male sterile cantaloupe plant comprising transforming the cantaloupe plant of claim 2 with a nucleic acid molecule.

19. A male sterile cantaloupe plant produced by the method of claim 18.

* * * * *